United States Patent
Zhang et al.

(10) Patent No.: US 10,752,549 B2
(45) Date of Patent: Aug. 25, 2020

(54) MODIFYING CEMENTITIOUS COMPOSITIONS USING KETONE ALCOHOL OIL WASTE

(71) Applicant: GCP Applied Technologies Inc., Cambridge, MA (US)

(72) Inventors: Shuqiang Zhang, Singapore (SG); Hua Zhong, Singapore (SG); Wee Fuk Lai, Singapore (SG); Felek Jachimowicz, Brookline, MA (US); Byong-wa Chun, Waban, MA (US); Yin-Zar Hnin, Singapore (SG)

(*) Notice: Subject to any disclaimer, the term of this patent is extended or adjusted under 35 U.S.C. 154(b) by 0 days.

(21) Appl. No.: 15/553,996

(22) PCT Filed: Feb. 27, 2015

(86) PCT No.: PCT/US2015/018089
§ 371 (c)(1),
(2) Date: Aug. 27, 2017

(87) PCT Pub. No.: WO2016/137508
PCT Pub. Date: Sep. 1, 2016

(65) Prior Publication Data
US 2018/0044240 A1    Feb. 15, 2018

(51) Int. Cl.
| | |
|---|---|
| C04B 28/02 | (2006.01) |
| C04B 40/00 | (2006.01) |
| C07C 45/33 | (2006.01) |
| C07C 29/50 | (2006.01) |
| C04B 7/48 | (2006.01) |
| C04B 24/00 | (2006.01) |
| C04B 24/02 | (2006.01) |
| C07C 29/48 | (2006.01) |
| C07C 45/27 | (2006.01) |
| C04B 103/52 | (2006.01) |
| C04B 103/40 | (2006.01) |
| C04B 103/50 | (2006.01) |
| C07C 31/135 | (2006.01) |
| C07C 49/11 | (2006.01) |

(52) U.S. Cl.
CPC ............ *C04B 28/02* (2013.01); *C04B 7/48* (2013.01); *C04B 24/003* (2013.01); *C04B 24/008* (2013.01); *C04B 24/02* (2013.01); *C04B 40/0039* (2013.01); *C07C 29/48* (2013.01); *C07C 29/50* (2013.01); *C07C 45/27* (2013.01); *C07C 45/33* (2013.01); *C04B 2103/408* (2013.01); *C04B 2103/50* (2013.01); *C04B 2103/52* (2013.01); *C07C 31/1355* (2013.01); *C07C 49/11* (2013.01); *Y02P 40/20* (2015.11); *Y02W 30/92* (2015.05)

(58) Field of Classification Search
CPC ....... C04B 7/48; C04B 24/003; C04B 24/008; C04B 24/02; C04B 28/02; C04B 40/0039; C04B 2103/50; C04B 2103/52; C04B 2103/408; C07C 29/48; C07C 29/50; C07C 31/1355; C07C 45/27; C07C 45/33; C07C 49/11
See application file for complete search history.

(56) References Cited

U.S. PATENT DOCUMENTS

| | | | |
|---|---|---|---|
| 3,047,629 A | 7/1962 | Steeman | |
| 4,453,978 A | 6/1984 | Okimura et al. | |
| 4,869,846 A | 9/1989 | Mouche et al. | |
| 5,654,352 A | 8/1997 | McDonald | |
| 6,160,183 A * | 12/2000 | Druliner | B01J 23/52 568/360 |
| 6,528,658 B1 * | 3/2003 | Miura | B01J 31/006 548/466 |
| 6,599,358 B1 | 7/2003 | Boggs | |
| 7,485,184 B2 | 2/2009 | Russell et al. | |
| 7,976,625 B2 | 7/2011 | Mao et al. | |
| 2005/0009959 A1 | 1/2005 | Bair et al. | |
| 2007/0039516 A1 | 2/2007 | Bandoh | |
| 2009/0258777 A1 | 10/2009 | Tardif et al. | |
| 2010/0286312 A1 | 11/2010 | Zhang et al. | |
| 2013/0019779 A1 | 1/2013 | Sebastien et al. | |
| 2015/0166412 A1 | 6/2015 | Stefan et al. | |

FOREIGN PATENT DOCUMENTS

| | | |
|---|---|---|
| EP | 2660217 | 11/2013 |
| RU | 2410345 | 1/2011 |
| SU | 1006424 A1 * | 3/1983 |
| SU | 1152947 | 4/1985 |
| SU | 1414825 | 8/1988 |
| SU | 1606490 | 11/1990 |
| SU | 1625850 | 2/1991 |
| SU | 1773903 A1 * | 11/1992 |
| WO | 2011086310 | 7/2011 |
| WO | 2013164212 | 11/2013 |

OTHER PUBLICATIONS

Copenheaver, Form PCT/ISA/210, International Search Report for PCT/US2015/018089, dated May 28, 2015, 2 pages.
Copenheaver, Form PCT/ISA/237, Written Opinion of the International Searching Authority for PCT/US2015/018089, dated May 28, 2015, 6 pages.
Gattinger, Supplementary European Search Report, EP application No. 15883599, dated Sep. 24, 2018, 8 pages.

* cited by examiner

*Primary Examiner* — Anthony J Green
(74) *Attorney, Agent, or Firm* — Craig K. Leon

(57) ABSTRACT

The present invention relates to modification of hydratable cement and cementitious materials, such as mortar cement and masonry or ready-mix concrete using ketone alcohol oil waste ("KAOW") material, obtained as an alkali-soluble liquor waste byproduct at a certain stage in the commercial production of cyclohexanol and cyclohexanone. Preferred applications for KAOW are in chemical admixture formulations whereby KAOW is used to substitute for a portion of a cement dispersant such as sodium lignosulfonate, sodium gluconate, or other conventional dispersant. Another preferred use is in mortar cement and masonry concrete units such as blocks, pavers, curbstones, and other concrete masonry units wherein air void systems advantageously foster freeze-thaw durability.

21 Claims, 1 Drawing Sheet

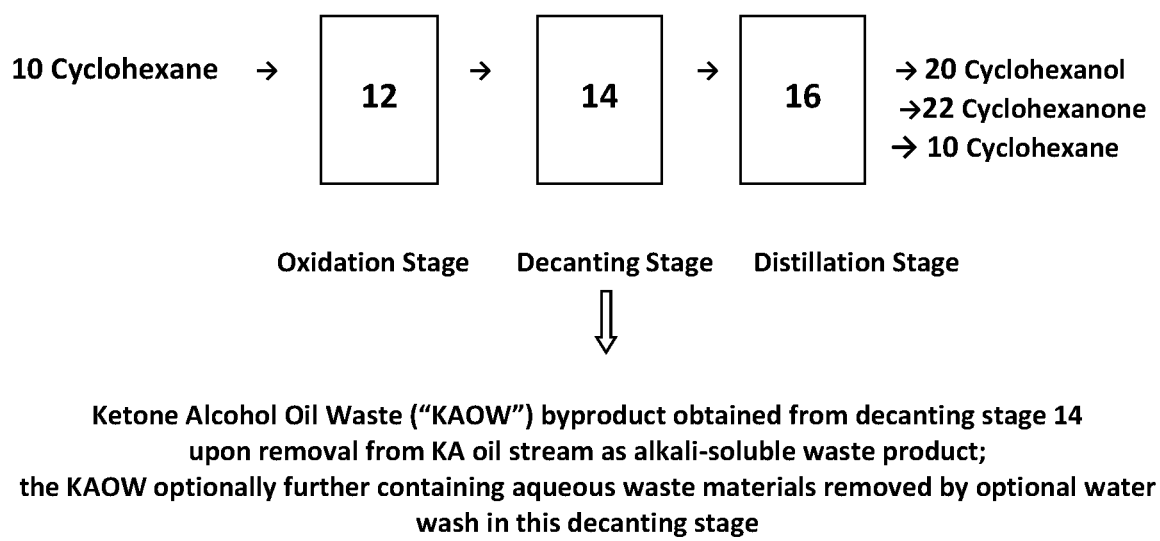

MODIFYING CEMENTITIOUS COMPOSITIONS USING KETONE ALCOHOL OIL WASTE

FIELD OF THE INVENTION

The invention relates to modification of hydratable cementitious compositions, and more particularly to modification of cement and concrete using "ketone alcohol oil waste" (KAOW) removed as byproduct material from the commercial production of cyclohexanone (ketone) and cyclohexanol (alcohol) from the starting material cyclohexane.

BACKGROUND OF THE INVENTION

It is known to employ byproducts obtained from commercial production of caprolactam, a precursor component used in manufacture of polyamide (nylon), for grinding of cements. In WO 2013/164212, Stefan et al. disclosed that byproducts obtained from the manufacture of caprolactam, wherein cyclohexanone is reacted with hydroxylamine, yielded the following materials: caprolactam (6-80% wt.), oligomers of caprolactam (2-20% wt.), aminocaproic acid (1.5-30% wt.), and alkali metal hydroxides (1-20% wt.), among others. See WO 2013/164212 at pages 5-6. Grinding additives containing caprolactam and aminocaproic acid were said to increase compressive strength of the cured cement product.

It is also known to use by-products from caprolactam production to increase late strength (after 28 days) in concrete mixes. See SU 1 424 825 and SU 1 606 490 (cited by Stefan et al. in WO 2013/164212 at page 3, ll. 19-21).

The present inventors have discovered a novel application in cement and concrete for byproduct material removed as an alkali-soluble waste from the ketone alcohol oil stream during commercial production of cyclohexanone (a ketone) and cyclohexanol (an alcohol). This waste material is to herein as ketone alcohol oil waste ("KAOW").

SUMMARY OF THE INVENTION

The present invention provides a novel additive composition and method for modifying cementitious materials using a waste byproduct, referred to herein as ketone alcohol oil waste (KAOW), which is removed as alkali-soluble waste material from the commercial production of cyclohexanone (a ketone) and cyclohexanol (an alcohol), a process that can otherwise be referred to as the ketone alcohol oil production process.

The ketone alcohol oil ("KA oil") production process comprises three basic stages: (i) cyclohexane is oxidized to produce a stream of cyclohexanone, cyclohexanol, and byproducts (hereinafter "oxidation stage"); (ii) the post-oxidation KA oil stream is then subjected to a caustic treatment (e.g., sodium hydroxide) to remove alkali-soluble waste from the supernatant oil phase which contains the cyclohexanone and cyclohexanol stream (hereinafter "decanting stage"); and (iii) the cyclohexanone and cyclohexanol stream is then subjected to distillation wherein cyclohexane is further removed using a first column separator (the cyclohexane may be re-circulated into the oxidation stage 12) and the stream may be further subjected to a second column to separate high boiling point materials from the cyclohexanone and cyclohexanol stream (hereinafter "distillation stage") which then may be used in downstream industrial processing (e.g., production of caprolactam).

The KAOW byproduct obtained from the caustic treatment wash may also contain water-soluble byproducts (e.g., glycols) removed using a water wash during the decanting stage, and this water wash may be employed before or after the caustic treatment wash.

The present inventors have surprisingly discovered that the KAOW byproduct containing the alkali-soluble waste material, regardless of whether it also contains water-soluble materials removed using the optional water wash, is useful for modifying hydratable cementitious compositions, particularly mortar cement, masonry concrete units (e.g., blocks, pavers), and ready-mix concrete.

Moreover, the present inventors have discovered that KAOW helps to extend the use of conventional cement dispersants when used in masonry cements and concrete, optionally with at least one air detraining agent ("ADA") in accordance with the preference of the user). Although various conventional cement dispersants are envisioned to be combinable with KAOW, the present inventors prefer sodium lignosulfonate, sodium gluconate, or a mixture thereof. For example, it is envisioned by the inventors that KAOW can be used to substitute for a considerable portion of the lignosulfonate, gluconate, or other conventional dispersant used in an admixture formulation.

An exemplary additive composition of the present invention for modifying a hydratable cementitious composition, thus comprises:

(A) at least one cement dispersant for dispersing hydratable cementitious particles within an aqueous environment;

(B) a ketone alcohol oil waste ("KAOW") byproduct obtained from commercial production of cyclohexanone and cyclohexanol, the commercial process comprising the following sequential stages (i) through (iii) as follows:

(i) oxidation stage wherein cyclohexane is oxidized to provide a stream of cyclohexanol, cyclohexanone, and other byproducts, (ii) decanting stage wherein the stream of cyclohexanol, cyclohexanone, and byproducts produced by the oxidation stage is subjected to a caustic agent wash (e.g., sodium hydroxide, calcium hydroxide, lime (calcium oxide), sodium carbonate (or soda ash), and/or other highly alkaline material, optionally with cobalt salts, chromium salts) to remove alkali-soluble waste material thereby obtaining KAOW from the post-oxidation stream (and optionally this caustic treatment can be preceded or followed by a water wash to remove water-soluble products which may optionally be added to the KAOW); and (iii) distillation stage wherein the cyclohexanol/cyclohexanone/byproduct stream provided by the decanting stage (ii) is provided into at least one separation column for recovering any residual cyclohexane (which may be removed and recirculated back to the oxidation stage (i)) and/or for removing high-boiling point material from the cyclohexanol/cyclohexanone/byproduct stream;

wherein the KAOW byproduct removed (as alkali-soluble waste in the caustic/alkaline treatment wash and optionally including the aqueous waste material removed by the prior water wash) from the decanting stage (ii) comprises at least four of the following sodium salts of C1 to C6 organic acids selected from the groups consisting of sodium hydroxide, sodium carbonate, sodium bicarbonate, sodium formate, sodium butyrate, sodium caproate, sodium glutarate, sodium adipate, sodium valerate, and sodium malonate, and derivatives thereof; and wherein the components (A) and (B) are provided in the weight ratio (A:B) of 25-75:75-25.

Another exemplary additive composition of the present invention further comprises, as component "(C)," an air detraining agent which is used in the amount of (C)/(A)+(B) based on percentage of total dry weight of components (A) and (B). The present inventors discovered that KAOW byproduct when used in combination with one or more cement dispersants can introduce a useful amount of entrainable air which is believed to be suitable for durability enhancement in mortar cements and also in concrete, whether in ready-mix or concrete masonry unit form (e.g., as blocks, pavers, slabs, panels, curbs, etc.)

The present invention also provides cement and cementitious compositions comprising the above-described KAOW-containing additive composition, as well as methods for modifying cement and cementitious materials, including mortar cement and concrete, wherein the KAOW-containing additive composition is combined with cement or cementitious materials (e.g., cement and fly ash), optionally with aggregates, or such as during manufacture of cement or cementitious materials ground from cement clinker, with or without fly ash or other supplemental cementitious materials.

In other exemplary embodiments, it is not necessary for the KAOW to be combined with or used with cement dispersant, or in any proportion with respect to a cement dispersant. The KAOW may be used, in another exemplary embodiment, in the intergrinding manufacture process whereby clinker is ground to produce finished cement, and the KAOW may be used in combination with a grinding additive.

Exemplary cement grinding additive compositions, useful as cement grinding additives or mortar cement additives, comprise KAOW in combination with diethylene glycol (DIEG), N,N-bis(2-hydroxyethyl)-2-hydroxypropylamine (DEIPA), or mixture thereof. In still further exemplary embodiments, the KAOW can be combined with fly ash, including carbon-containing fly ashes, separately or in combination with cement and concrete, to confer air entrainment properties into hydratable cementitious mixtures which might otherwise have difficulty incorporating beneficial air voids.

In still further embodiments, KAOW can be combined with manufactured sand, fly ash, or mixtures thereof, as well as with other materials which would be benefitted by the ability of KAOW to incorporate useful air voids into cement or concrete.

Further advantages and features of the present invention may be described in further detail hereinafter.

BRIEF DESCRIPTION OF THE DRAWING

The Figure is a schematic block diagram of the commercial production of cyclohexanone (a ketone) and cyclohexanol (an alcohol) from the starting material cyclohexane, whereby a ketone alcohol oil waste (KAOW) material may be obtained in the form of a post-oxidation, alkali-soluble waste byproduct (optionally including post-oxidation aqueous wash waste) removed from the cyclohexanol/cyclohexanone/byproduct stream.

DETAILED DESCRIPTION OF EXEMPLARY EMBODIMENTS

The term "cement" as used for describing the present invention includes hydratable cement such as Portland cement which is produced by pulverizing clinker consisting of hydraulic calcium silicates and one or more forms of calcium sulfate (e.g., gypsum) as an interground additive. Typically, Portland cement is combined with one or more supplemental cementitious materials, such as fly ash (e.g., Class C), granulated blast furnace slag, limestone, natural pozzolan, or mixtures thereof, and provided as a blend. The term "cement" may also include supplemental cementitious materials that were interground with Portland cement during manufacture, such as fly ash (e.g., Class C). The term "cementitious" may refer to cement alone or in combination with one or more such supplemental cementitious materials.

The term "hydratable" refers to cement or cementitious materials that are hardened by chemical interaction with water. Portland cement clinker is a partially fused mass primarily composed of hydratable calcium silicates. The calcium silicates are essentially a mixture of tricalcium silicate ($3CaO.SiO_2$ "$C_3S$" in cement chemist notation) and dicalcium silicate ($2CaO.SiO_2$, "$C_2S$") in which the former is the dominant form, with lesser amounts of tricalcium aluminate ($3CaO.Al_2O_3$, "$C_3A$") and tetracalcium aluminoferrite ($4CaO.Al_2O_3.Fe_2O_3$, "$C_4AF$"). See e.g., Dodson, Vance H., Concrete Admixtures (Van Nostrand Reinhold, New York N.Y. 1990), page 1.

Typically, Portland cement is combined with one or more other cementitious materials, such as the foregoing supplemental cementitious materials (e.g., fly ash), and provided as a blend. Cement or cementitious materials are typically combined with fine aggregate (e.g., sand) to provide a "mortar" cement; they may be combined with both fine aggregate and coarse aggregate (e.g., crushed stone or gravel) to provide "concrete." The term "concrete" may be used herein to refer to all cementitious materials which include aggregates.

As explained in the Summary section above, exemplary additives of the present invention for modifying cement and cementitious materials, including mortar cement and concrete, comprise a ketone alcohol oil waste (KAOW) byproduct obtained from the commercial production of cyclohexanone and cyclohexanone from the oxidation of cyclohexane, and is in the form of a post-oxidation, alkali-soluble waste byproduct (and optionally further including post-oxidation, aqueous wash waste material) removed from the cyclohexanol/cyclohexanone/byproduct stream.

The Figure illustrates diagrammatically a commercial process wherein cyclohexane 10 is subjected to an "oxidation stage" (see block designated at 12) which generates a stream of cyclohexanol/cyclohexanone/byproducts which is then subjected to a "decanting stage" (see block designated at 14) from which waste products including ketone alcohol oil waste (KAOW) byproduct are removed using a caustic treatment aqueous wash (to remove alkali-soluble materials) from the cyclohexanol/cyclohexanone/byproducts stream which is then subjected to a distillation stage (see block designated at 16). The term "alkali-soluble" as used herein refers to materials which are aqueous soluble at pH greater than 7 and preferably up to pH of 10 and greater.

As explained by authoritative sources such as Ullmann's Encyclopedia of Industrial Chemistry, Wiley Online Library, Michael Tuttle Musser, Author, (Published Online Oct. 14, 2011, http://onlinelibrary.wiley.com/doi/10.1002/14356007.a08 217.pub2/pdf) both cyclohexanol and cyclohexanone are produced on a large commercial scale, and the vast majority of these compounds and their mixtures is consumed in the production of caprolactam and adipic acid, which are then used thereafter as intermediates in the manufacture of polyamide (nylon) fibers, textiles, and related applications.

The oxidation of cyclohexane to cyclohexanol and cyclohexanone was first produced on an industrial scale, Musser explains, by transition metal-catalyzed liquid-phase air oxidation of cyclohexane, which provides a mixture of cyclohexanol and cyclohexanone. This was done as early as the 1940's using a series of agitated reactors at 140-180° C. and at 0.8-2 MPa, although a single tower oxidizer could be used. In this oxidation scheme, some initially formed cyclohexyl hydroperoxide ($C_6H_{12}+O_2 \rightarrow C_6H_{11}OOH$) is converted in the oxidizer(s) to cyclohexanol, cyclohexanone, and byproducts (3 $C_6H_{11}OOH \rightarrow 2$ $C_6H_{11}OH + C_6H_{10}O + H_2O + O_2$+byproducts). Musser explained that intermediate cyclohexyl hydroperoxide and the cyclohexanol and cyclohexanone products are more readily oxidized than cyclohexane, such that conversion of the latter in the oxidizers were ideally kept low to maximize yield. In addition to yielding alcohol, ketone, and hydroperoxides, the oxidation step also generated a wide range of mono- and dicarboxlic acids, esters, aldehydes, and other oxygenated materials.

Muller explained that processes for oxidation of cyclohexane subsequently designed in the 1950s by Scientific Design (now Halcon International), employed a series of air oxidation vessels wherein cyclohexyl hydroperoxide, trapped in the form of a cyclohexyl perborate ester (18 $C_6H_{12}+9O_2+2H_3B_3O_6 \rightarrow 6$ $B(OOC_6H_{11})_3+12$ $H_2O$), is reacted with added amounts of cyclohexane in the air oxidizer to yield borate ester and additional cyclohexanol ($B(OOC_6H_{11})_3+3$ $C_6H_{12} \rightarrow B(OC_6H_{11})_3+3$ $C_6H_{11}OH$). The ester is then subsequently hydrolyzed to cyclohexanol and boric acid ($B(OC_6H_{11})_3+3$ $H_2O \rightarrow 3$ $C_6H_{11}OH + H_3BO_3$). The boric acid is dehydrated to metaboric acid and recycled to the air oxidizer (3 $H_3BO_3 \rightarrow H_3B_3O_6+3$ $H_2O$). Musser further explains that while this newer oxidation process is similar to the metal-catalyzed oxidation process (as explained in the foregoing paragraph), the cyclohexyl rings are protected from further attack. This boric acid process is purportedly characterized by higher yield of cyclohexanol and cyclohexanone, as well as a higher alcohol to ketone ratio (which could be as high as 10:1). Musser notes that this Halcon oxidation process is licensed to several companies around the world, and that the major producers using this technology (as of 2011) were Solutia, DuPont (UK), Bayer, and Mitsubishi.

The oxidation stage (designated at block 12 in the Figure) as contemplated by the present inventors can involve the earlier air oxidation of cyclohexane process, or, more preferably, the boric acid modified oxidation of cyclohexane (e.g., Halcon oxidation), as explained in the preceding paragraph. In the oxidation stage, it is also optional to remove hexane diol during the oxidation stage 12. As shown in the Figure, the cyclohexanone/cyclohexanol/byproduct stream provided by the oxidation stage (designated at block 12) is then subjected to the decanting stage (designated at block 14) from which alkali-soluble KAOW material is removed from the KA oil stream; and a subsequent KA oil distillation stage (designated at block 16).

In the decanting stage 14 in the Figure, the cyclohexanone/cyclohexanol/byproduct stream (or "KA oil" stream) provided by the oxidation stage 12 is typically subjected to caustic treatment (e.g., highly alkaline treatment using e.g., calcium hydroxide, sodium hydroxide, calcium oxide (lime), sodium carbonate (or soda ash), or other caustic agents or mixtures thereof, optionally with salts, e.g., cobalt, chromium) in a reactor to remove the ketone alcohol oil waste (KAOW) as an alkali-soluble byproduct material. This KAOW material may optionally also include water-soluble material (e.g., glycols) from the KA oil stream by an optional water wash that precedes and/or follows the caustic treatment.

Thus, KAOW contains a mixture of sodium salts of C1-C6 organic acids and may contain a small amount of sodium hydroxide (or other caustic material used in the caustic treatment portion of the decanting stage 14), and, as mentioned above, optional water-soluble materials removed as part of an optional water wash during the decanting stage.

It may also be noted here that in decanting stage 14, as shown in the Figure, the KAOW byproduct which is separated from the cyclohexanone/cyclohexanol/byproduct stream may be subjected to distillation (to remove further materials for industrial use); but distillation of the KAOW product separated from the KA oil stream should not to be confused with the distillation stage 16 wherein the KA oil (i.e., the supernatant, decanted oily stream containing the cyclohexanone and cyclohexanol) is subjected to one or more distillation separator columns to remove residual cyclohexane and/or high boiling point materials. In the distillation stage 16 (as shown in the drawing), residual cyclohexane 12 removed from the cyclohexanone/cyclohexanol stream may be recycled back into the oxidation stage 12. The post-distillation cyclohexanol 20 and cyclohexanone 22 can then be used for other industrial purposes (e.g., as intermediate material for synthesis of caprolactam and adipic acid, which are in turn precursor/intermediates for manufacturing polyamide (nylon) materials).

Thus, an exemplary additive composition of the present invention for modifying a hydratable cementitious composition, comprises: (A) at least one cement dispersant for dispersing hydratable cementitious particles within an aqueous environment, such as a glycol (e.g., diethylene glycol), a glycerol, an alkanolamine (e.g., N,N-bis(2-hydroxyethyl)-2-hydroxypropylamine (DEIPA)), an organic acid not derived from nylon polymer manufacturing, a lignosulfonate (e.g., sodium lignosulfonate), a gluconate (e.g., sodium gluconate), a naphthalene sulfonate formaldehyde condensate, an acetone sulfonate formaldehyde condensate, a polycarboxylate polymer (e.g., a superplasticizing comb-type polycarboxylate polymer), a hydroxycarboxylate compound, a carbohydrate, a fermentation molasses, or derivatives or mixtures thereof); and (B) a ketone alcohol oil waste ("KAOW") byproduct obtained from a commercial production process whereby cyclohexanol and cyclohexanone are produced from oxidation of cyclohexane.

Preferred cement dispersants include lignosulfonate, a gluconate, or derivative of mixture thereof, and most preferred are sodium lignosulfonate, sodium gluconate, or mixture thereof. When lignosulfonate is present, it is preferred also that an air detraining agent (preferably a nonionic defoaming agent) be employed. It is further mentioned by the present inventors that KAOW may be used with gluconate without necessarily requiring the use of an air detraining agent.

The relative amount of cement dispersant of component (A) and the KAOW of component (B) may be used in any desired ratios, although a preferred weight ratio (A:B) is 25-75:75-25. Amounts and percentages of materials shall be understood to be expressed herein based on dry weight solids unless otherwise indicated. The weight amount of the KAOW component will be further understood to be based on non-volatile constituents of the KAOW material.

Further exemplary additive compositions of the present invention may also include, as component "(C)," an air detraining agent being present, based on the amount of aforesaid components (A) and (B), in the amount of (C)/(A)+(B) based on percentage of total dry weight of components (A) and (B). In further exemplary embodiments, the component (C) percentage is based on weight of non-volatile constituents of components (A) and (B).

The component (B) ketone alcohol oil waste ("KAOW") byproduct, as discussed above, is obtained from the commercial production process whereby cyclohexanol and cyclohexanone are produced from cyclohexane. The production process can be described as comprising (i) an oxidation stage wherein cyclohexane is oxidized to provide a stream of cyclohexanol, cyclohexanone, and other byproducts (optionally hexane diol and other polyols can be removed in accordance with various industrial practices); (ii) decanting stage wherein the stream of cyclohexanol, cyclohexanone, and byproducts produced by the oxidation stage are subjected to a caustic treatment using a highly alkaline material (e.g., calcium hydroxide, sodium hydroxide, sodium carbonate (soda ash), calcium oxide, lime, or mixtures thereof, optionally with salts) to remove alkali-soluble waste material thereby obtaining KAOW from the post-oxidation stream (and optionally a water wash before and/or after the caustic treatment to remove water soluble materials); and (iii) a distillation stage wherein the cyclohexanol/cyclohexanone stream treated in decanting stage (ii) is provided into at least one separation column for recovering any residual cyclohexane 12 (which can be recycled into the oxidation stage) and/or for removing high-boiling point material from the cyclohexanol/cyclohexanone/byproduct stream.

In exemplary embodiments of the present invention, the KAOW byproduct removed from the decanting stage (ii) may be characterized as comprising at least four of the following sodium salts of C1 to C6 organic acids selected from the groups consisting of sodium hydroxide, sodium carbonate, sodium bicarbonate, sodium formate, sodium butyrate, sodium caproate, sodium glutarate, sodium adipate, sodium valerate, and sodium malonate, and derivatives thereof.

In further exemplary embodiments, where the KOAW byproduct removed from the decanting stage (ii), the KAOW may further comprise aqueous soluble waste material which was removed from the cyclohexanone/cyclohexanol/byproduct (KA oil) stream by a water wash treatment that occurs before and/or after the caustic treatment, in addition to the alkali-soluble materials removed in the post-caustic-treatment alkaline wash.

In further exemplary embodiment of the invention, the KAOW byproduct will contain carboxylic acid groups.

To avoid any confusion with prior art byproducts obtained from the later-industrial-stage caprolactam processes, the present inventors prefer to use KAOW byproduct materials which are substantially free of caprolactam and aminocaproic acid which both contain nitrogen. Hence, preferred embodiments of the additive compositions of the present invention comprise KAOW byproduct material which substantially contains no caprolactam and substantially no aminocaproic acid. Hence, further exemplary embodiments of the KAOW material will contain substantially no or negligible amounts nitrogen (or, in other words, KAOW material incorporated into any additive or admixture should comprise nitrogen in an amount no more than 0-1.0 percent based on total dry solids (of non-volatile materials) in the KAOW byproduct obtained from the decanting stage (ii) as previously discussed.

While it is contemplated by the present inventors that a number of conventional air detraining agents (ADAs) be employed in combination with KAOW, preferred ADAs are triisobutylphosphate and alkoxylated defoamers (e.g., C16-C18 alkyl alcohol ethoxylate propoxylate), but the most preferred ADAs would likely depend upon end use application and the other mixture components employed. Other preferred ADAs are non-ionic in nature.

The present invention also provides cementitious compositions, which comprise: a hydratable cement or cementitious material in combination with the above described KAOW byproduct material. An exemplary cement or concrete composition of the present invention comprises a hydratable cement, fly ash (e.g., Class C fly ash), and KAOW or an additive composition comprising at least one cement dispersant and KAOW), optionally with at least one air detraining agent. Exemplary concretes comprise hydratable cement, aggregate, (e.g., sand and/or coarse aggregate), and the KAOW byproduct material.

The present invention also provides methods for modifying a cementitious material, comprising: combining a hydratable cement or cementitous material (e.g., a supplemental cementitious material such as fly ash), or mixture thereof, with KAOW or an additive composition comprising at least one cement dispersant and KAOW.

The present invention also provides a method wherein KAOW may be combined with a cement grinding additive (e.g., DIEG, DEIPA, or combination thereof) introduced into a manufacturing process for grinding cement clinker, the additive composition being used in an amount of 0.01% to 0.3% based on dry solids weight percentage based on weight of cement. The cement may be made with fly ash (e.g., Class C) as an inter-ground component with cement or mixed with the fly ash after grinding.

In a further exemplary method of the invention, KAOW material (such as may be in the form of an additive composition also comprising a cement dispersant, an air detraining agent, or mixture thereof) is combined with a hydratable cementitious material and aggregate material, the additive composition being used in an amount of 0.3% to 1.3% based on dry solids weight of cement.

While the invention is described herein using a limited number of embodiments, these specific embodiments are not intended to limit the scope of the invention as otherwise described and claimed herein. Modification and variations from the described embodiments exist. More specifically, the following examples are given as a specific illustration of embodiments of the claimed invention. It should be understood that the invention is not limited to the specific details set forth in the examples. All parts and percentages in the examples, as well as in the remainder of the specification, are by percentage weight unless otherwise specified.

EXAMPLE 1

KAOW materials obtained as waste byproducts from the KA oil production process explained above provide a number of chemical components, primarily sodium salts, which are found to be helpful in modifying hydratable cementitious compositions.

The present inventors have characterized KAOW as comprising at least four of the following sodium salts of C1 to C6 organic acids selected from the groups consisting of sodium hydroxide, sodium carbonate, sodium bicarbonate, sodium formate, sodium butyrate, sodium caproate, sodium glutarate, sodium adipate, sodium valerate, and sodium malonate, and derivatives thereof; and this is based on their analysis of various KAOW materials. For example, typical examples of KAOW compositions are shown in Table 1 and Table 2 below.

TABLE 1

(Typical KA Oil byproduct (KAOW) composition)
(Data from MSDS provided by DSM Chemicals North America, Inc)

| Name | CAS # | % by Weight |
|---|---|---|
| Water | 7732-18-5 | 75.0-80.0 |
| Sodium Hydroxide | 1310-73-2 | 0.0-1.9 |
| Sodium Carbonate | 497-19-8 | 3.5-8.0 |
| Sodium Bicarbonate | 144-55-8 | 0.0-3.0 |
| Sodium Formate | 141-53-7 | 0.5-1.5 |
| Sodium Acetate | 127-09-3 | 0.2-1.0 |
| Sodium Butyrate | 156-54-7 | 1.0-3.0 |
| Sodium Caproate | 10051-44-2 | 0.4-1.5 |
| Sodium Glutarate | 13521-83-0 | 0.8-2.0 |
| Sodium Adipate | 7486-38-6 | 0.8-2.5 |
| Sodium Valerate | 6106-41-8 | 1.0-2.5 |
| Sodium Malonate | 141-95-7 | 0.0-1.5 |

TABLE 2

(Typical KA Oil byproduct (KAOW) composition 2)
(Data from MSDS provided by UBE Chemicals (Asia) Public Company Limited)

| Chemical name | CAS No. | Concentration (%) |
|---|---|---|
| Water | 7732-18-5 | 78 |
| Organic content | — | 15 |
| Sodium carbonate | 497-19-8 | 2.6 |
| Sodium hydrogen carbonate | 144-55-8 | 2.2 |
| Sodium hydroxide | 1310-73-2 | 0.5 |

Table 3 and Table 4 show the actual analytical results of the KAOW sample obtained from a supplier (UBE Thailand).

TABLE 3

Typical KA Oil byproduct (KAOW) composition 3
(chemical analysis of KAOW sample from UBE Thailand)

| Component | Percent of weight of sample |
|---|---|
| Aliphatic Carboxylic Acids as sodium salts (see Table 4) | 16% |
| Other Carboxylic acids as sodium salts (by difference)* | approx. 4% |
| Nitrogen containing compound** | Less than 1% |
| Sodium hydroxide/carbonate*** | approx. 2% |

*Titration of the sample indicated the presence of more carboxylic acid groups than can be accounted for the sum of aliphatic carboxylic acids listed in table above. Therefore the difference between the total solids and the sum of determined materials is listed as "other carboxylic acids". Hence, exemplary additive compositions of the invention based on KAOW material include carboxylic acids.
**Nitrogen was measured at 0.1083% (by Galbraith Laboratories). The nature of the nitrogen containing compound is not known. Therefore, it is a mere estimate that the nitrogen containing component is present at not more than 1%. Hence, exemplary additive compositions of the invention based on KAOW material which does not include substantial amounts of nitrogen (i.e., the KAOW contains 0-1% nitrogen in total).
***The excess sodium may be present as sodium hydroxide/carbonate.

TABLE 4

(HPLC results of Aliphatic Carboxylic Acids as sodium salts)
(analysis of KAOW sample from UBE Thailand)

| propanoic | butyric | pentanoic | hexanoic | Acetic | formic |
|---|---|---|---|---|---|
| 1.3% | 1% | 6% | 4% | 1.5% | 1.8% |

The analysis confirms the information contained in the Material Safety Data Sheet of UBE Industries (Asia). The present inventors note that as between the KAOW material sourced from UBE and the KAOW material sourced from DSM, the identity of chemical constituents appears to be nearly identical, although the relative quantities of constituents suggest small variations. The variations appear so minor, and no appreciable difference in the performance of the KAOW material, when used in cement and concrete, is observed by the present inventors.

EXAMPLE 2

Concrete Slump and Setting Time Testing

Cement dispersants increase fluidity of cement paste, mortar and concrete. Such dispersants are also called water reducers because they allow less water to be used in mortar cement or concrete without loss of slump (a measure of consistency or workability). Many cement additives permit the use of less water to obtain the same slump, or the attainment of a higher slump at given water content, or the use of less Portland cement to realize the same compressive strength. The performance requirements for water reducing admixtures are specified in ASTM Method C494-92, "Standard Specifications for Chemical Admixtures for Concrete." In ASTM C494-92, a water reducing admixture is defined as an admixture that reduces the quantity of mixing water required to produce concrete of a given consistency by at least 5%.

The present inventors discovered that KAOW has great benefits when used as or in chemical admixture formulations for modifying properties such as slump in concrete, whether in ready-mix concrete or in concrete masonry units (e.g., blocks, pavers), alone or in combination with conventional cement dispersants.

The testing in concrete was performed as follows. Concrete sample dosage with KAOW and an air detraining agent (commercially available from Dow under the trade name Surfonic LF-68) is used in dosages as shown in the table below. Chemical tests were conducted in accordance with SS EN 934. The cement used was a commercial bagged cement (Engro 50-kg bag). Fine and coarse aggregates used were local available natural sand and crushed granite with 5-25 mm size. Concrete mix design is shown in Table 5.

TABLE 5

Mix Design: Ordinary Portland Cement:Water:Sand:Stone - 20 mm = 362 kg:203 kg:900 kg:1100 kg (per cubic meter) Defoamer = Huntsman SURFONIC ™ LF68

| S/N | KAOW % by wt based on OPC | Defoamer | Slump @ 5 min. | Slump @60 min. | Air Content % @ 5 min. | Setting Time Initial Hours | Setting Time Final Hours |
|---|---|---|---|---|---|---|---|
| 1 | Plain Mix | — | 85 | 60 | 1.1 | 3.28 | 5.58 |
| 2 | 35%-0.01 | — | 90 | 60 | 1.3 | 3.3 | 6.03 |
| 3 | 35%-0.05 | — | 115 | 80 | 2.0 | 3.54 | 6.24 |
| 4 | 35%-0.075 | 0.1% | 125 | 80 | 2.6 | 3.48 | 6.15 |

TABLE 5-continued

Mix Design: Ordinary Portland Cement:Water:Sand:Stone – 20 mm = 362 kg:203 kg:900 kg:1100 kg (per cubic meter) Defoamer = Huntsman SURFONIC ™ LF68

| S/N | KAOW % by wt based on OPC | Defoamer | Slump @ 5 min. | Slump @60 min. | Air Content % @ 5 min. | Setting Time Initial Hours | Setting Time Final Hours |
|---|---|---|---|---|---|---|---|
| 5 | 35%-0.125 | 0.15% | 140 | 70 | 2.9 | 3.52 | 6.22 |
| 6 | 35%-0.25 | 0.5% | 140 | 80 | 3.4 | 3.48 | 6.18 |

KAOW (solid) was found, at dosage 0.01% to 0.3% by weight of cement, has good effect on the dispersing effect of cement and concrete. The (optimized dispersing effect) results can most preferably be achieved when the dosage of KAOW is 0.05% to 0.13% by weight of cement.

EXAMPLE 3

KAOW with Lignosulfonate Formulation Concrete Test

The present inventors used KAOW material in formulation with lignosulfonate. Concrete testing was performed as follows: Concrete sample dosage with lignosulfonate, KAOW, and defoamer (LF68) according to the dosage shown in the table below. Chemical tests were conducted were according to SS EN 934 method. Cement used was commercial bagged cement (Lafarge Cement 50-kg bag), and fine and coarse aggregates used were local available natural sand and crushed granite with 5-25 mm size. Concrete mix design is as below.

TABLE 6

Mix Design: Lafarge Ordinary Portland Cement:Water:Sand:stone – 20 mm = 320 kg:220 kg:880 kg:1000 kg (per cubic meter). Defoamer = SURFONIC ® LF68 from Huntsman Corporation.

| Mix No. | Admixtures | Dosage | Slump @ 3 min. | Slump @60 min. | Air Content % @ 3 min. | Setting Time Initial Hours | Setting Time Final Hours | Compr. Strength 3 days (MPa) | Compr. Strength 7 days (MPa) | Compr. Strength 28 days (MPa) |
|---|---|---|---|---|---|---|---|---|---|---|
| 1 | Ligno (40%) | 0.30 | 145 | 93 | 1.7 | 6.3 | 9.13 | 13.0 | 19.1 | 21.3 |
| 2 | Ligno (40%) | 0.23 | 140 | 91 | 2.4 | 6.01 | 8.53 | 13.6 | 19.0 | 21.5 |
|   | KAOW (35%) | 0.07 |   |   |   |   |   |   |   |   |
|   | Defoamer | 0.30 |   |   |   |   |   |   |   |   |
| 3 | Ligno (40%) | 0.15 | 130 | 80 | 1.6 | 6.04 | 8.48 | 13.4 | 18.7 | 21.0 |
|   | KAOW (35%) | 0.15 |   |   |   |   |   |   |   |   |
|   | Defoamer | 0.50 |   |   |   |   |   |   |   |   |
| 4 | Ligno (40%) | 0.07 | 110 | 60 | 1.5 | 6.06 | 8.34 | 13.7 | 18.9 | 22.4 |
|   | KAOW (35%) | 0.23 |   |   |   |   |   |   |   |   |
|   | Defoamer | 1.20 |   |   |   |   |   |   |   |   |

When KAOW is used to replace 25% to 75% by weight (solids) of the lignosulfonate, the present inventors discovered that the admixture provided similar dispersing efficiency compared to using 100% of lignosulfonate. For example, an optimized dispersing efficiency is discovered to be achieved when replacement is about 25%.

At 25% lignin replacement, KAOW can achieve similar strength when it is combined with 0.3 to 1.3% by weight of KAOW. The air detraining agent (or defoaming surfactant) used was SURFONIC® LF68 available from Huntsman Chemical, which is based on fatty alcohol alkoxylates. Hence, exemplary embodiments of the present invention may comprise KAOW in combination with fatty alcohol alkoxylate air detraining agents, although the present inventors believe that based on the foregoing results, non-ionic defoaming agents could be suitable used with KAOW in cementitious compositions.

EXAMPLE 4

KAOW Gluconate Formulation Concrete Mixing Test

The present inventors also used KAOW material in formulations with a gluconate. The concrete testing was as follows: the concrete sample dosage with the gluconate, KAOW, and defoamer (SURFONIC® LF68) was done according to the dosage shown in table 7 below. Chemical tests were conducted were according to SS EN 934 method. The cement used was commercial bagged cement (Lafarge 50-kg cement bag), fly ash used was from a supplier in Thailand and fine and coarse aggregates used were local available natural sand and crushed granite with 5-25 mm size. Concrete mix design is shown in Table 7 below.

TABLE 7

Mix Design: Lafarge Ordinary Portland Cement:Fly ash:Water:Sand:Stone − 20 mm = 210 kg:110 kg:220 kg:880 kg:1000 kg (per cubic meter)

| Mix No. | Admixtures | Dosage | Slump @ 3 min. | Slump @60 min. | Air Content % @ 3 min. | Setting Time Initial Hours | Setting Time Final Hours | Compr. Strength 3 day | Compr. Strength 7 days | Compr. Strength 28 days |
|---|---|---|---|---|---|---|---|---|---|---|
| 1 | Gluconate (20%) | 0.27 | 180 | 105 | 0.8 | 9.32 | 12.02 | 8.60 | 10.60 | 16.05 |
| 2 | KAOW (35%) | 0.45 | 175 | 95 | 1.5 | 8041 | 11.11 | 8.80 | 10.10 | 15.65 |
| 3 | Gluconate (20%) KAOW (35%) | 0.20 0.17 | 180 | 95 | 1 | 8.39 | 11.09 | 9.35 | 10.30 | 16.05 |
| 4 | Gluconate (20%) KAOW (35%) | 0.20 0.38 | 180 | 110 | 1.3 | 7.27 | 9.57 | 8.55 | 10.25 | 14.7 |
| 5 | KAOW (35%) | 0.83 | 185 | 115 | 2.5 | 8.02 | 10.32 | 7.95 | 9.60 | 15.05 |

When the present inventors replaced 25% of gluconate using KAOW (based on percentage solids), they discovered that this provided a similar dispersing efficiency efficiency in the masonry cement compared to using 100% gluconate. This dosage efficiency can be achieved if 4 to 10 times the amount of KAOW is used. For 25% gluconate replacement, KAOW can achieve similar strength compared to 100% gluconate without the need of air detraining agent (defoamer).

EXAMPLE 5

KAOW and Lignosulfoante Formulation Concrete Mixing

Another KAOW material (obtained from a different source compared to the foregoing examples) was also tested in concrete mixes. The concrete testing was done as follows: The concrete sample dosage with lignosulfonate, KAOW, and air detraining agent (SURFONIC® LF-68 from Huntsman Chemical) was used in accordance with the dosages shown in table 8 below.

Chemical tests were conducted were according to SS EN 934 method. Cement used was commercial bagged cement (Liulihe Cement 50-kg bag), fly ash used was obtained from a supplier in China, and fine and coarse aggregates used were local available natural sand and gravel with 5-20 mm size. The concrete mix design is shown in Table 8 below.

TABLE 8

Mix Design: OPC:Fly Ash:Water:Sand:Stone = 270 kg:130 kg;230 kg:850 kg:900 kg (per cubic meter)
Defoamer: Surfonic ® LF-68 (Huntsman)

| Mix No. | Admixtures | Dosage | Slump @ 3 min. | Slump @ 60 min. | Air Content % @ 3 min. |
|---|---|---|---|---|---|
| 1 | Lignosulfonate (40%) Defoamer | 0.30 1.20 | 120 | — | 1.4 |
| 2 | Lignosulfonate (40%) KAOW (35%) Defoamer | 0.23 0.09 1.20 | 155 | — | 1.7 |
| 3 | Lignosulfonate (40%) KAOW (35%) Defoamer | 0.23 0.35 1.20 | 165 | — | 2 |

The present inventors confirmed that KAOW byproduct material obtained from a different source performed similarly to the other sourced KAOW material.

EXAMPLE 6

KAOW Material Used in Cement Grinding at Various Dosages

The present inventors found that when KAOW was added to cement clinker, the grinding efficiency was improved, and thus discover that KAOW can function as a cement grinding aid. Therefore, one embodiment of the present invention is a grinding additive composition for grinding cement and cementitious materials.

The inventor also discovered that KAOW can be effectively formulated with existing grinding additive chemicals, including without limitation: glycols, glycerol, alkanolamines, and organic acids. Therefore, another embodiment of the present invention is KAOW cement grinding additive composition wherein KAOW is formulated with one or more cement grinding aids selected from the group consists of glycols, glycerol, alkanolamines, and organic acids. The weight % of KAOW byproduct can also be 25-75% based on weight total solids of active ingredients in the cement grinding additive composition that is formulated using the KAOW material.

One of the challenges the inventors identified is that when KAOW dosage is relativity high, KAOW has a tendency to entrain air upon mixing the treated cement with water. Therefore, it is preferred that KAOW containing cement grinding additives contain a defoamer. For cement grinding, the present inventors discovered that triisobutylphosphate may be advantageously used at a dosage of 1-5% by weight based on non-volatile component of KAOW material.

Exemplary KAOW-containing cement grinding additive composition of the present invention comprise KAOW, diethyleneglycol, glycerin, and triisobutylphosphate. The preferred dosage of the KAOW grinding aid composition is at the dosage 0.01% to 0.3% as a non-volatile solid by weight of cement clinker. It was discovered that KAOW-containing grinding additive compositions reduce the energy of grinding; and that the resultant cement is of higher quality compared to cement not prepared using the additive.

Cement was ground using diethylene glycol and KAOW in varying dosages. Grinding material was 2000 grams of clinker (50% >4.72 mm, 30% 2.36-4.72 mm, 20% <2.36 mm), and grinding involved 3500 constant revolutions in laboratory mill. Data is shown below:

TABLE 9

| Grind | DIEG dosage ppm | KAOW dosage (ppm) | SSA (cm$^2$/g) | R45 (%) |
|---|---|---|---|---|
| 1 | 100 | | 3669 | 4.4 |
| 2 | | 100 | 3612 | 5.2 |
| 3 | 200 | | 3726 | 3.4 |
| 4 | | 200 | 3754 | 3.2 |
| 5 | 300 | | 3744 | 2.4 |
| 6 | | 300 | 3707 | 2.2 |
| 7 | 500 | | 3726 | 1.5 |
| 8 | | 500 | 3763 | 1.34 |

EXAMPLE 7

KAOW in Hot Grinding at Various Dosages

The present inventors also tested KAOW in hot grinding as follows. The grinding material was 2000 grams of clinker (50% >4.72 mm, 30% 2.36-4.72 mm, 20% <2.36 mm) and 105 grams gypsum, and grinding was done at constant revolutions for total of 3500 rounds. The sample materials were dosed directly on grinding materials, heated in oven at 100° C., and the data and results of the mixing are shown in Table 10 below.

TABLE 10

| Grind | Sample | Dosage (active ppm) | SSA (cm$^2$/g) | R45 (%) | Strength (MPa) 1-day | 3-day | 7-day | 28-day |
|---|---|---|---|---|---|---|---|---|
| 1 | Blank | 0 | 3394 | 7.6 | 11.4 | 23.6 | 33.5 | 53.1 |
| 2 | KAOW | 300 | 3534 | 6.0 | 12.4 | 24.1 | 34.4 | 49.1 |
| 3 | KAOW | 600 | 3573 | 4.8 | 13.6 | 26.2 | 36.3 | 47.4 |
| 4 | KAOW | 1000 | 3650 | 2.6 | 15.2 | 30.2 | 38.2 | 48.5 |
| 5 | DIEG | 300 | 3554 | 4.0 | 16.0 | 28.4 | 38.2 | 49.9 |

EXAMPLE 8

KAOW in Hot Grinding at Various Dosages with Triisobutylphosphate Defoamer

The present inventors also tested KAOW along with TiBP defoaming agent in hot grinding as follows. The grinding material was 2000 grams of clinker (50% >4.72 mm, 30% 2.36-4.72 mm, 20% <2.36 mm) and 105 grams gypsum. Grinding was done using constant revolutions totaling 3500 rounds. The sample additives were dosed directly onto the grinding materials, and the mix was heated in oven at 100° C. then ground. Amount of defoamer (TiBP) is based on KAOW. The results of the mixing are shown in Table 11 below.

TABLE 11

| Sample | Dosage (active ppm) | Defoamer (%) | SSA (cm$^2$/g) | R45 (%) | Air | Flow (mm) | Strength (MPa) 1-day | 3-day | 7-day | 28-day |
|---|---|---|---|---|---|---|---|---|---|---|
| 1 Blank | 0 | 0 | 3374 | 7.8 | 2.6 | 226 | 14.94 | 27.90 | 38.31 | 52.0 |
| 2 KAOW | 300 | 3 | 3455 | 5 | 2.8 | 219 | 16.27 | 31.44 | 39.63 | 53.9 |
| 3 KAOW | 600 | 3 | 3435 | 4.2 | 3.2 | 225 | 16.84 | 31.23 | 40.31 | 51.3 |
| 4 KAOW | 1000 | 3 | 3599 | 2.8 | 3.0 | 219 | 16.51 | 32.71 | 42.62 | 54.1 |
| 5 DIEG | 300 | 0 | 3573 | 4.8 | 2.2 | 215 | 18.15 | 33.29 | 43.77 | 54.5 |

EXAMPLE 9

KAOW and DIEG Formulation Hot Grind at Various Dosages

The present inventors tested the use of KAOW with diethylene glycol (DIEG) at various dosages in hot grinding. The grinding material was 2500 grams of clinker (50% >4.72 mm, 30% 2.36-4.72 mm, 20% <2.36 mm) and 130 grams gypsum. Grinding revolution: 5500 rounds. Sample was blended into mixtures according to table below. Sample mixtures dosed on grinding materials, mix and grind at constant revolution. The data and results are shown below in Table 12.

TABLE 12

| Grind | DIEG % (active) | KAOW % (active) | DIEG dosage (ppm) | KAOW dosage (ppm) | SSA (cm$^2$/g) | R45 (%) |
|---|---|---|---|---|---|---|
| 1 | 100% | 0% | 50 | 0 | 3573 | 5.6 |
| 2 | 0% | 100% | 0 | 50 | 3799 | 4.4 |
| 3 | 75% | 25% | 37.5 | 12.5 | 3706 | 4.2 |
| 4 | 50% | 50% | 25 | 25 | 3688 | 4.6 |
| 5 | 25% | 75% | 12.5 | 37.5 | 3818 | 4.0 |
| 6 | 100% | 0% | 150 | 0 | 3943 | 4 |
| 7 | 0% | 100% | 0 | 150 | 3907 | 4 |
| 8 | 75% | 25% | 112.5 | 37.5 | 3995 | 4 |
| 9 | 50% | 50% | 75 | 75 | 3995 | 3.8 |
| 10 | 25% | 75% | 37.5 | 112.5 | 3995 | 3.8 |

EXAMPLE 13

KAOW and DIEG Formulation Mortar Test with Triisobutylphosphate Defoamer

The present inventors tested the use of KAOW with diethylene glycol (DIEG) in mortar cement. The mortar test was performed using cement sample dosage with DIEG, KAOW and TiBP according to the dosage shown in the table 13 below. The mortar mix was formulated in accordance with EN196 method. Air was measured using 400 mL weighing cup. The Cement used is commercial bagged cement (Lafarge 50-kg bag). The data and results are shown below in Table 13.

TABLE 13

| Grind | Sample dosage | | TiBP dosage (% KAOW) | Mortar weight (g) | Air (%) | Strength (MPa) | | |
|---|---|---|---|---|---|---|---|---|
| | DIEG (ppm) | KAOW (ppm) | | | | 1-day | 3-day | 7-day |
| 1 | 300 | 0 | na | 899 | 2.5% | 12.6 | 27.7 | 43.1 |
| 2 | 0 | 300 | 4.4% | 900 | 2.4% | 11.9 | 30.3 | 45.0 |
| 3 | 0 | 600 | 4.8% | 904 | 2.0% | 11.6 | 29.5 | 44.4 |
| 4 | 0 | 1000 | 4.4% | 900 | 2.4% | 12.3 | 31.6 | 46.4 |
| 5 | 0 | 1000 | 3.0% | 897 | 2.7% | 11.1 | 28.8 | 43.5 |
| 6 | 0 | 1000 | 1.9% | 890 | 3.5% | 11.6 | 29.2 | 45.0 |
| 7 | 0 | 1000 | 0.8% | 874 | 5.2% | 10.7 | 27.5 | 41.4 |
| 8 | 300 | 0 | na | 898 | 2.6% | 12.4 | 28.3 | 42.5 |

The foregoing description, tables, and drawing are provided for the purpose of explanation and not to be construed as limiting the invention. While the invention has been described with reference to preferred embodiments or preferred methods, it is understood that the words which have been used herein are words of description and illustration, rather than words of limitation. Furthermore, although the invention has been described herein with reference to particular formulations, structures, methods, and embodiments, the invention is not intended to be limited to the particulars disclosed herein, as the invention extends to all formulations, structures, methods and uses that are within the scope of the appended claims. Those skilled in the art, having benefit of the teachings herein, may affect numerous modifications and changes without departing from the scope and spirit of the invention as defined by the appended claims.

We claim:

1. An additive composition for modifying a hydratable cementitious composition, comprising:
   (A) at least one cement dispersant for dispersing hydratable cementitious particles within an aqueous environment;
   (B) a ketone alcohol oil waste ("KAOW") byproduct obtained from a commercial production process whereby cyclohexanol and cyclohexanone are produced from cyclohexane, the commercial process comprising the following stages (i) through (iii) as follows:
      (i) oxidation stage wherein cyclohexane is oxidized to provide a stream of cyclohexanol, cyclohexanone, and other byproducts,
      (ii) decanting stage wherein the stream of cyclohexanol, cyclohexanone, and byproducts produced by the oxidation stage is subjected to caustic treatment to remove alkali-soluble waste material thereby obtaining KAOW from the post-oxidation stream, and
      (iii) distillation stage wherein the cyclohexanol/cyclohexanone/byproduct stream treated in decanting stage (ii) is provided into at least one separation column for recovering any residual cyclohexane or for removing high-boiling point material from the cyclohexanol/cyclohexanone/byproduct stream;
   wherein the KAOW byproduct removed from the decanting stage (ii) comprises at least four sodium compounds selected from the group consisting of sodium hydroxide, sodium carbonate, sodium bicarbonate, sodium formate, sodium butyrate, sodium caproate, sodium glutarate, sodium adipate, sodium valerate, and sodium malonate, and derivatives thereof; and
   wherein the above components (A) and (B) are provided in the weight ratio (A:B) of 25-75:75-25.

2. The additive composition of claim 1 wherein KAOW obtained in the decanting stage further contains water soluble material removed from the stream of cyclohexanol and cyclohexanone by a water wash treatment which precedes or follows the caustic treatment.

3. The additive composition of claim 1 further comprising as component "(C)" an air detraining agent being present in the amount of (C)/(A)+(B) based on percentage of total dry weight of components (A) and (B).

4. The additive composition of claim 3 wherein component (C) percentage is based on weight of non-volatile constituents of components (A) and (B).

5. The additive composition of claim 1 wherein the at least one cement dispersant of component (A) comprises a glycol, glycerol, alkanolamine, lignosulfonate, gluconate, naphthalene sulfonate formaldehyde condensate, acetone sulfonate formaldehyde condensate, a polycarboxylate polymer, hydroxycarboxylate compound, a carbohydrate, a fermentation molasses, or a derivative or mixture thereof.

6. The additive composition of claim 1 wherein the at least one cement dispersant of component (A) comprises a lignosulfonate, a gluconate, or derivative of mixture thereof.

7. The additive composition of claim 6 wherein the at least one cement dispersant of component (A) is sodium lignosulfonate, sodium gluconate, or mixture thereof.

8. The additive composition of claim 1 wherein the KAOW byproduct of component (B) comprises at least sodium hydroxide and sodium carbonate.

9. The additive composition of claim 1 wherein the KAOW byproduct of component (B) comprises carboxylic acid groups.

10. The additive composition of claim 1 wherein the KAOW byproduct of component (B) comprises nitrogen in an amount less than one percent total weight.

11. The additive composition of claim 2 wherein the air detraining agent is selected from the group consisting of triisobutylphosphate and C16-C18 ethoxylate propoxylate alkyl alcohol.

12. The additive composition of claim 2 wherein the air detraining agent is triisobutylphosphate.

13. A cementitious composition comprising: cement, fly ash, and the additive composition of claim 1.

14. The cementitious composition of claim 13 further comprising sand, coarse aggregate, or mixture thereof.

15. A method for modifying a cementitious material, comprising: combining a hydratable cement, supplemental cementitious material, or mixture thereof with the additive composition of claim 1.

16. The method of claim 15 wherein the additive composition is combined with a hydratable cementitious material and aggregate material, the additive composition being used in an amount of 0.3% to 1.3% based on dry solids weight percentage based on weight of hydratable cementitious material.

17. A cementitious composition comprising: hydratable cement and a ketone alcohol oil waste ("KAOW") byproduct obtained as an alkali-soluble waste from a commercial production process whereby cyclohexanol and cyclohexanone are produced from cyclohexane, the commercial process comprising the following stages (i) through (iii) as follows:
  (i) oxidation stage wherein cyclohexane is oxidized to provide a stream of cyclohexanol, cyclohexanone, and other byproducts,
  (ii) decanting stage wherein the stream of cyclohexanol, cyclohexanone, and byproducts produced by the oxidation stage is subjected to caustic treatment to remove alkali-soluble waste material thereby obtaining KAOW from the post-oxidation stream, and
  (iii) distillation stage wherein the cyclohexanol/cyclohexanone/byproduct stream treated in decanting stage (ii) is provided into at least one separation column for recovering any residual cyclohexane or for removing high-boiling point material from the cyclohexanol/cyclohexanone/ byproduct stream;

wherein the KAOW byproduct removed from the decanting stage (ii) comprises at least four sodium compounds selected from the group consisting of sodium hydroxide, sodium carbonate, sodium bicarbonate, sodium formate, sodium butyrate, sodium caproate, sodium glutarate, sodium adipate, sodium valerate, and sodium malonate, and derivatives thereof.

18. The cementitious composition of claim 17 wherein KAOW obtained in the decanting stage further contains water soluble material removed from the stream of cyclohexanol and cyclohexanone by a water wash treatment which precedes or follows the caustic treatment.

19. The cementitious composition of claim 17 further comprising fly ash, manufactured sand, or mixture thereof.

20. The cementitious composition of claim 17 further comprising carbon-bearing fly ash.

21. The cementitious composition of claim 17 further comprising an air detraining agent.

* * * * *